(12) United States Patent
Han et al.

(10) Patent No.: US 11,885,804 B2
(45) Date of Patent: Jan. 30, 2024

(54) APPLICATION OF ERH GENE IN THE PREPARATION OF BLADDER CANCER DIAGNOSIS AND TREATMENT PRODUCTS

(71) Applicant: XUZHOU CENTRAL HOSPITAL, Jiangsu (CN)

(72) Inventors: Conghui Han, Jiangsu (CN); Qian Lv, Jiangsu (CN); Kun Pang, Jiangsu (CN); Lin Hao, Jiangsu (CN); Ying Liu, Jiangsu (CN)

(73) Assignee: XUZHOU CENTRAL HOSPITAL, Jiangsu (CN)

( * ) Notice: Subject to any disclaimer, the term of this patent is extended or adjusted under 35 U.S.C. 154(b) by 81 days.

(21) Appl. No.: 17/454,836

(22) Filed: Nov. 15, 2021

(65) Prior Publication Data

US 2022/0065859 A1 Mar. 3, 2022

Related U.S. Application Data

(63) Continuation of application No. 16/090,658, filed as application No. PCT/CN2017/085951 on May 25, 2017, now abandoned.

(30) Foreign Application Priority Data

Feb. 13, 2017 (CN) .......................... 201710076979.4

(51) Int. Cl.
| | | |
|---|---|---|
| *C12N 15/11* | (2006.01) | |
| *G01N 33/574* | (2006.01) | |
| *A61K 31/713* | (2006.01) | |
| *C12N 15/113* | (2010.01) | |
| *G01N 33/68* | (2006.01) | |
| *C12Q 1/6886* | (2018.01) | |
| *G01N 33/577* | (2006.01) | |

(52) U.S. Cl.
CPC ..... *G01N 33/57407* (2013.01); *A61K 31/713* (2013.01); *C12N 15/1135* (2013.01); *G01N 33/68* (2013.01); *C12N 2310/14* (2013.01); *C12Q 1/6886* (2013.01); *C12Q 2600/136* (2013.01); *C12Q 2600/158* (2013.01); *G01N 33/577* (2013.01); *G01N 2800/52* (2013.01)

(58) Field of Classification Search
CPC .......................... A61K 31/713; C12N 2310/14
See application file for complete search history.

(56) References Cited

U.S. PATENT DOCUMENTS

| | | |
|---|---|---|
| 9,902,998 B2 | 2/2018 | Alcaraz Asensio et al. |
| 2014/0323342 A1 | 10/2014 | Chapman et al. |

FOREIGN PATENT DOCUMENTS

| | | |
|---|---|---|
| CN | 104450893 A | 3/2015 |
| CN | 105586422 A | 5/2016 |
| WO | 2013074837 A1 | 5/2013 |
| WO | 2014118334 A1 | 8/2014 |

OTHER PUBLICATIONS

Kompier et al., FGFR3, HRAS, KRAS, NRAS and PIK3CA Mutations in Bladder Cancer and Their Potential as Biomarkers for Surveillance and Therapy, PLoS ONE, 2010, vol. 5, issue 11, e13821: 1-13. (Year: 2010).*
Weng et al., "Evolutionarily conserved protein ERH controls CENP-E mRNA splicing and is required for the survival al KRAS mutant cancer cells", PNAS Plus, 2012, pp. E3659-E3667, vol. 109, No. 52.

* cited by examiner

*Primary Examiner* — Ekaterina Poliakova-Georgantas
(74) *Attorney, Agent, or Firm* — NKL Law; Allen Xue (57) ABSTRACT

The invention relates to the application of the ERH gene in the preparation of bladder cancer diagnosis and treatment products. The ERH gene is found to have a good correlation with bladder cancer. In addition, an RNA interference vector is constructed to perform cell function experiments to study the effect of ERH gene on the proliferation and clonality of bladder cancer cells. The present invention provides a research basis for clinical diagnosis and treatment of bladder cancer and has a good application prospect.

3 Claims, 6 Drawing Sheets

Specification includes a Sequence Listing.

APPLICATION OF ERH GENE IN THE PREPARATION OF BLADDER CANCER DIAGNOSIS AND TREATMENT PRODUCTS

CROSS REFERENCE TO RELATED APPLICATIONS

This application is a continuation of U.S. application Ser. No. 16/090,658 filed Oct. 2, 2018, which is a U.S. national phase of International Application No. PCT/CN2017/085951 filed May 25, 2017, which claims priority to Chinese Patent Application No. 201710076979.4 filed Feb. 13, 2017, the disclosure of which are hereby incorporated by reference in their entireties.

INCORPORATION OF SEQUENCE LISTING

This application contains a sequence listing submitted in Computer Readable Form (CRF). The CFR file containing the sequence listing entitled "PA630-0004_ST25.txt", which was created on Nov. 12, 2021, and is 5,108 bytes in size. The information in the sequence listing is incorporated herein by reference in its entirety.

TECHNICAL FIELD

The present invention relates to the field of biomedicine, in particular to the field of cancer treatment and diagnosis, and more specifically to the application of ERH gene in the preparation of bladder cancer diagnosis and treatment products, and the application of ERH gene or its expression product as a molecular marker in the detection of bladder cancer, and as a target molecule developed for antitumor drugs, which weakening the growth of bladder cancer cells.

BACKGROUND OF RELATED ART

Bladder cancer is a common disease in the clinical practice of urology, and it is also a common tumor in the urinary system, with high morbidity and mortality. The traditional diagnostic methods for bladder cancer include routine urine tests, urine exfoliative cytology, cystoscopy, KUB plain film, CT, MR, and other imaging findings that are associated with the development of the disease, invasion and metastasis. In recent years, molecular targeted diagnosis and treatment of bladder cancer have received more and more attention in clinical practice as an important mean for comprehensive diagnosis and treatment of tumors and emerging therapeutic models. Multiple tumor markers such as MKI67, EGFR, ERBB2, TP53, PCNA and ETS-2 have been reported to be closely related to bladder cancer. In view of the dangers of bladder cancer, especially the high recurrence rate of non-invasive bladder cancer, makes early diagnosis, recurrence monitoring, and extensive routine screening necessary, and to find a target of molecular diagnosis and treatment of bladder cancer with high sensitivity and specificity is of great significance.

The present invention has detected bladder cancer tissues and paracancerous tissues of the patients and found that ERH has good correlation with bladder cancer and can be used to prepare auxiliary diagnosis and treatment preparations for bladder cancer. In addition, cell function experiments such as RNA interference were performed to study the effect of ERH on the proliferation of bladder cancer cells. The present invention provides a research basis for the diagnosis and treatment of clinical bladder cancer.

SUMMARY OF THE INVENTION

A method for diagnosing bladder cancer or the propensity to develop bladder cancer, comprising the following steps:
(1) detecting an expression level of ERH in biological samples;
(2) Elevated expression of ERH is associated with bladder cancer.

Further, the expression level of ERH in biological samples is performed by detecting an amino acid sequence that is at least 80% homologous to part or all of the mRNA of the ERH and/or to part or all of the amino acid sequence encoding the ERH protein. Preferably, at least 85%, 90%, 91%, 92%, 93%, 94%, 95%, 96%, 97%, 98%, 99% or more homologous sequences.

Further, detecting the ERH gene expression levels in biological samples is performed by detecting part or all of the ERH mRNA and/or detecting part or all of the amino acid sequence encoding the ERH protein.

Further, ERH gene expression levels in biological samples is detected by fluorescence quantitative PCR method or gene chip method or the expression of ERH protein in biological samples is detected by immunization method. Preferably, the immunization method of detecting the ERH protein expression is performed by Western blot or ELISA or colloidal gold assay.

The ERH gene expression levels in biological samples suffering from bladder cancer or a tendency to develop bladder cancer is higher than that of a normal control tissue or a paracancerous tissue.

According to another aspect of the present invention, an application of the detection of the expression level of ERH gene or protein in the preparation of bladder cancer diagnostic formulations is provided.

Further, the bladder cancer diagnostic formulations include detection of ERH gene expression level in a sample using a fluorescent quantitative PCR method and a gene chip method.

Fluorescence quantitative PCR method is the application of fluorescent dyes or fluorescently labeled probes specific to trace the PCR products, real-time online monitor the reaction process, analyze the product combined with the corresponding software, and calculate the initial concentration of the sample template to be measured.

Gene chips, also called DNAmicroarray, can be classified into three main types: 1) Nucleic acid probes or cDNA fragments immobilized on the surface of polymer substrates (nylon membranes, nitrocellulose membranes, etc.), isotope-labeled target genes are hybridized to them and detected by radiographic techniques; 2) A DNA probe array immobilized on a glass plate by a spotting method and detected by hybridization with a fluorescently labeled target gene; 3) An oligonucleotide probe array synthesized directly on a hard surface such as glass and hybridized with a fluorescently labeled target gene for detection.

The product used for the fluorescence quantitative PCR method to detect the ERH gene in bladder cancer contains a pair of primers that specifically amplify the ERH gene; the gene chip includes a probe that hybridizes to the nucleic acid sequence of the ERH gene.

Further, diagnostic reagents for bladder cancer include the application of immunization method to detect the expression level of ERH protein in bladder cancer. Preferably, the immunological method for the detection of ERH protein expression in bladder cancer is western blot or ELISA or colloidal gold detection method.

Enzyme-linked immunosorbent assay (ELISA) is a technique in which known antigens or antibodies are adsorbed on the surface of a solid-phase carrier, and enzyme-labeled antigen-antibody reactions are performed on a solid-phase surface. ELISA test kits can be divided into indirect method, double-antibody sandwich method, competition method, two-step one-step method, capture method to measure IgM antibodies, and ELISA using avidin and biotin according to the detection purpose and operation procedure. The chromogenic substrate in the ELISA test kit can be selected from horseradish peroxidase (HRP) or alkaline phosphatase (AP).

Commonly used immune colloidal gold technique include: (1) Immunogold light microscopy staining: the cell suspension smears or tissue sections may be stained with colloidal gold-labeled antibodies, or may be marked with a silver developer on the basis of the colloidal gold label, so that the reduced silver atoms are deposited on the surface of the labeled gold particles, and the sensitivity of colloidal gold labels can be significantly enhanced; (2) Immunogold electron microscopy staining: the colloidal gold-labeled antibodies or anti-antibodies can be combined with negatively-exposed virus samples or tissue ultrathin sections, and then negatively stained, which can be used for virus morphology observations and virus detection; (3) Spot immunogold filtration uses a microporous membrane as a vector, the antigen or antibody is firstly spotted on the membrane, after blocking, the sample to be examined is added, after washing, antibodies labeled with the colloidal gold are used to detect the corresponding antigen or antibody; (4) Colloidal gold immunochromatography: fixes specific antigens or antibodies on the membrane in strips, and the colloidal gold labeling reagent (antibody) adsorbs on the binding pad, after the sample to be tested is added to the sample pad at one end of the test strip, it is moved forward by capillary action to dissolve the colloidal gold labeling reagents on the binding pad and react with each other, when moving to a fixed antigen or antibody region, the conjugate of the analyte and the gold labeling reagent is specifically bound to it and is retained, and is accumulated on the detection tape, and the coloration result can be observed with the naked eye.

Further, the ELISA method for detecting ERH protein is an ELISA detection kit. Commercially available ERH monoclonal antibodies can be used as antibodies in the kit. Further, the kit includes: a solid phase carrier coated with an ERH monoclonal antibody, an enzyme-labeled antibody, an enzyme substrate, a protein standard, a negative control, a diluent, a washing solution, and an enzyme reaction-terminating solution.

Further, the colloidal gold method for detecting ERH proteins is a detection kit, and commercially available ERH monoclonal antibodies can be used as antibodies. Further, the colloidal gold detection kit employs colloidal gold immunochromatography or colloidal gold filtration. Further, the colloidal gold detection kit has an anti-ERH monoclonal antibody in the detection zone (T) spray point on the nitrocellulose membrane, and an immunoglobulin IgG in the quality control zone (C) spray point.

According to another aspect of the present invention, a gene detection kit for bladder cancer is provided. The kit detects the gene ERH using a specific upstream primer and a downstream primer. The upstream primer sequence is SEQ ID NO. 11 and the downstream primer sequence is SEQ ID NO.12.

Further, the PCR kit is suitable for various types of fluorescence quantitative gene amplification instruments currently on the market.

Further, the fluorescent quantitative PCR kit components include: specific primers, internal reference primers, and fluorescent quantitative PCR reaction solutions. The specific primers include an upstream primer and a downstream primer, the upstream primer sequence is SEQ ID NO.11 and the downstream primer sequence is SEQ ID NO.12. The internal reference primer is a GAPDH internal reference primer, the upstream primer sequence is SEQ ID NO.13, and the downstream primer sequence is SEQ ID NO.14.

According to another aspect of the present invention, a bladder cancer protein detection kit is provided. The kit detects the ERH protein. Further, the kit also includes other detection reagents.

According to another aspect of the present invention, a gene chip for detecting bladder cancer is provided. The gene chip includes a probe that hybridizes to a nucleic acid sequence of the ERH gene. The diagnosis or detection of the bladder cancer in the subject of the present invention is mainly through the measurement of a biological sample derived from a patient, including cells, tissues, etc., and can be blood or urine.

According to another aspect of the present invention, a method for screening a compound for treating or preventing bladder cancer is provided which comprises the following steps:
(1) providing a polypeptide that comprises at least 80% homologous sequence to an ERH amino acid sequence;
(2) detecting a binding activity between a compound to be tested and the polypeptide; and
(3) selecting a compound that binds to the polypeptide.

Preferably, the polypeptide and the ERH amino acid sequence are at least 85%, 90%, 91%, 92%, 93%, 94%, 95%, 96%, 97%, 98%, 99% or more homologous sequences.

According to another aspect of the present invention, a method for screening a compound for treating or preventing bladder cancer is provided which comprises the following steps:
(1) contacting one of plurality of compounds with cells that express sequences that are at least 80% homologous to the ERH nucleotide sequence; and
(2) selecting a compound that has a reduced level of expression of a sequence having at least 80% homology with the ERH nucleotide sequence expressed by the cell.

Preferably, the cell expression is at least 85%, 90%, 91%, 92%, 93%, 94%, 95%, 96%, 97%, 98%, 99% or more homologous to the ERH nucleotide sequence.

Further, the cells are bladder cancer cells.

According to another aspect of the present invention, a method for screening a compound for treating or preventing bladder cancer is provided which comprises the following steps:
(1) contacting a compound with a cell introduced into a vector, the vector comprising a transcriptional regulatory region of the ERH gene and a reporter gene expressed under the control of the transcriptional regulatory region;
(2) determining the expression level or activity of the reporter gene; and
(3) selecting a compound that reduces the expression level or activity of the reporter gene.

According to another aspect of the present invention, a method of treating or preventing bladder cancer is provided. The method could reduce the expression of ERH in a subject.

Further, the expression level of ERH is reduced by antisense oligonucleotides or interfering RNA targeting ERH.

RNA interference refers to post-transcriptional gene silencing due to target mRNA degradation or translational inhibition. There are typically 19-25 bases of single-stranded or double-stranded RNA, ie, small interfering RNAs (siRNAs), also known as interfering RNAs. RNA interference can effectively and specifically block the expression of homologous genes in the body, promote the degradation of homologous mRNA and induce cells to exhibit a specific gene deletion phenotype. After the siRNA design is completed, a direct synthesis method or construction of an siRNA expression vector may be used. The prepared siRNA may be transfected with cells by means of calcium phosphate coprecipitation, electroporation, DEAE-dextran and polybrene, microinjection or gene gun, and cationic liposome reagents.

Antisense oligonucleotides (asON) refer to short nucleotide fragments that bind to specific DNA and RNA in a base-pair complementary manner and prevent transcription and translation thereof.

Preferably, the interfering RNA includes a sense strand and an antisense strand that are complementary to each other, the sense strand being 19-25 consecutive nucleotides in the ERH mRNA, and preferably, the interfering RNA is targeted to SEQ ID NO.15; More preferably, the sequences of the interfering RNA are SEQ ID NO.18 and SEQ ID NO.19.

According to another aspect of the present invention, a method of treating or preventing bladder cancer is provided which comprises the step of administering to a subject a pharmaceutically effective amount of an antibody or an immunologically active fragment thereof. The antibody or immunologically active fragment binds to ERH protein or inhibits the activity of ERH protein.

According to another aspect of the present invention, a composition for treating or preventing bladder cancer is provided which comprises a pharmaceutically effective amount of an antisense oligonucleotide or interfering RNA against ERH as an active ingredient, and further comprises a pharmaceutically acceptable carrier.

According to another aspect of the present invention, a composition for treating or preventing bladder cancer is provided which comprises a pharmaceutically effective amount of an antibody or an immunologically active fragment that binds to an ERH protein, and further includes a pharmaceutically acceptable carrier.

The pharmaceutically acceptable carrier to be included in the present invention is a carrier which is commonly used at the time of preparation and contains lactose, dextrose, sucrose, sorbitol, mannitol, starch, arabic rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, stearic acid magnesium, mineral oil and the like, but not the carrier should not limited thereto.

In addition to the above ingredients, the composition of the present invention may also contain a lubricant, a moisturizer, a sweetener, a flavoring agent, an emulsifier, a suspending agent, a preservative, and the like. The pharmacologically acceptable carriers and preparations are described in detail in the Remington's Pharmacy Book.

The composition of the present invention can be administered orally or non-orally, and when administered non-orally, it can be administered intravenously, intranasally, locally, intracerebroventricularly, intraspinal injection, subcutaneously, intraperitoneally, transdermal administration, etc.

The suitable dose of the composition of the present invention is based on factors such as the preparation method, administration method, patient's age, weight, sex, pathological state, food, administration time, administration route, excretion rate, and reaction sensitivity. A variety of prescriptions can be performed. In general, skilled doctors can easily determine and prescribe the desired therapeutically or prophylactically effective dose.

The composition of the present invention is formulated according to a method easily practicable by a person of ordinary skill in the art, by using pharmaceutically acceptable carriers and/or excipients, so that the composition can be prepared in a unit dosage form or internally made in a multi-capacity container. In this case, the dosage form is in the form of a solution, suspension or emulsion in an oily or aqueous medium, or it may be in the form of an extract, a powder, a granule, a tablet or a capsule, and may also include a dispersant or a stabilizer.

According to another aspect of the present invention, an application of the ERH gene or protein inhibitor in the preparation of anti-bladder cancer preparations is provided.

Further, an anti-bladder cancer preparation refers to a preparation that can suppress the expression level of ERH gene in bladder cancer cells. It is well known in the art that anti-bladder cancer preparations may employ one or more of the following methods to inhibit the expression level of ERH in bladder cancer cells: by activating an inhibitor gene of the ERH gene, activating a protein that inhibits expression of an ERH gene, introducing an siRNA that inhibits ERH expression, introducing an antisense oligonucleotide that inhibits ERH expression, introducing a vector that inhibits ERH expression, and activating a microRNA that promotes degradation of ERH mRNA, introducing molecules that promote degradation of ERH proteins, suppressing the expression of factors and proteins that promote the expression level of ERH genes, inhibiting the activity of promoter or enhancer of ERH genes, enhancing the activity of ERH gene silencer, introducing antibodies or immunologically active fragments that bind to ERH proteins.

Preferably, the interfering RNA includes a sense strand and an antisense strand that are complementary to each other, the sense strand being 19-25 consecutive nucleotides in the ERH mRNA, and preferably, the interfering RNA is targeted to SEQ ID NO.15; more preferably, the sequences of the interfering RNA are SEQ ID NO. 18 and SEQ ID NO.19.

Preferably, the inhibitor of the ERH gene or ERH protein is a compound screened using a screening method for the aforementioned compound for treating or preventing bladder cancer.

Another aspect of the present invention is to provide an anti-bladder cancer preparation, anti-bladder cancer preparation inhibits the expression level of ERH gene in bladder cancer cells.

Further, anti-bladder cancer preparations inhibit the proliferation or metastasis of bladder cancer cells. Further, anti-bladder cancer preparations inhibit the formation of tumors of bladder cancer cells.

According to another aspect of the present invention, a method for inducing anti-tumor immunity is provided which comprises contacting the antigen-presenting cells with a polypeptide encoded by an ERH, an ERH polynucleotide, or a vector comprising an ERH polynucleotide.

According to another aspect of the present invention, a diagnostic reagent for bladder cancer is provided which comprises primers for specifically amplifying the ERH gene, preferably, the primer sequences are SEQ ID NO.11 and SEQ ID NO.12.

Further, the bladder cancer diagnostic reagent further comprises primers for specifically amplifying MKI67, EGFR, ERBB2, TP53, and PCNA genes. Preferably, the primer sequences are SEQ ID NO.1 and SEQ ID NO.2; SEQ ID NO.3 and SEQ ID NO.4; SEQ ID NO.5 and SEQ ID NO.6; SEQ ID NO.7 and SEQ ID NO.8; SEQ ID NO. 9 and SEQ ID NO.10.

According to another aspect of the present invention, a bladder cancer diagnostic agent is provided which comprises a probe that hybridizes to a nucleic acid sequence of an ERH gene.

According to another aspect of the present invention, a bladder cancer diagnostic agent is provided which comprises an antibody or immunologically active fragment that binds to an ERH protein.

According to another aspect of the present invention, an interfering RNA is provided which comprises the complementary strands of sense and antisense strands, which is 19-25 contiguous nucleotides in the ERH mRNA. Preferably, the interfering RNA is SEQ ID NO.15 for the target; more preferably, the sequences of the interfering RNA are SEQ ID NO.18 and SEQ ID NO.19.

According to another aspect of the present invention, a vector is provided which contains a sequence encoding the aforementioned interfering RNA. Preferably, the vector is a lentiviral vector. More preferably, the vector is psc2903.

According to another aspect of the present invention, a cell is provided which comprises the above vector, preferably comprises the vector psc2903.

The term "bias" of bladder cancer as applied and in the context of the present invention covers a subject susceptible to bladder cancer and has a state of bladder cancer tendency, morbidity, tendency or sensitivity. The term also covers the subject's risk of getting bladder cancer.

The normal control tissue of the present invention refers to healthy individuals or individuals known not to have bladder cancer, and the level of ERH gene expression detected in the population is a control. Unless otherwise defined, all technical and scientific terms used herein have the same meaning as commonly understood by one of ordinary skill in the art to which this invention belongs.

DETAILED DESCRIPTION OF THE EMBODIMENT

The present invention is illustrated in detail in conjunction with the specific embodiments, and the embodiment has been explained to facilitate understanding of the present invention but not to limit the scope of the invention. Those of ordinary skill in the art can understand that various changes, modifications, substitutions and variations can be made to these embodiments without departing from the principle and spirit of the present invention, and the scope of the present invention is defined by the claims and their equivalents. The experimental methods that do not specify the specific conditions in the following examples are generally tested according to conventional conditions or according to the manufacturer's recommended conditions.

Example 1 Tissue Sample RNA Extraction and Fluorescence Quantitative PCR

Thirty-two pairs of samples of bladder cancer and paracancerous tissue were prepared. Case samples were confirmed by pathological examination. Sample RNA was extracted using TRIzol method, followed by agarose gel electrophoresis after RNA extraction, and RNA sample extraction was performed using the NanoDrop1000 spectrophotometer. Among them, 12 pairs of samples of cancer tissues and paracancerous tissues were all qualified for the test. See Table 1 for follow-up fluorescence quantitative detection experiments.

TABLE 1

| | | | RNA test results | | | | |
|---|---|---|---|---|---|---|---|
| Sample number | Concentration (ng/µl) | 260/280 | Sample Type | Sample No. | Concentration (ng/µl) | 260/280 | Sample Type |
| Cancer1 | 668.6 | 2.06 | RNA | Cancer7 | 400.7 | 2 | RNA |
| paracancerous 1 | 150 | 1.99 | RNA | Cancer adjacent 7 | 417.4 | 2.04 | RNA |
| Cancer 2 | 373.4 | 2.08 | RNA | Cancer 8 | 312.6 | 1.9 | RNA |
| paracancerous 2 | 246 | 2 | RNA | Cancer adjacent 8 | 209.5 | 1.9 | RNA |
| Cancer 3 | 378.5 | 1.97 | RNA | Cancer 9 | 440.7 | 1.9 | RNA |
| paracancerous 3 | 343.6 | 1.99 | RNA | Cancer adjacent 9 | 288.3 | 2.0 | RNA |
| Cancer 4 | 520.5 | 1.89 | RNA | Cancer 10 | 727.8 | 1.95 | RNA |
| paracancerous 4 | 458.3 | 2.02 | RNA | Cancer adjacent 10 | 496.4 | 2.06 | RNA |

TABLE 1-continued

RNA test results

| Sample number | Concentration (ng/μl) | 260/280 | Sample Type | Sample No. | Concentration (ng/μl) | 260/280 | Sample Type |
|---|---|---|---|---|---|---|---|
| Cancer 5 | 297.1 | 1.99 | RNA | Cancer 11 | 728 | 1.95 | RNA |
| paracancerous 5 | 560.3 | 2.01 | RNA | Cancer adjacent 11 | 496.2 | 2.06 | RNA |
| Cancer 6 | 379.6 | 2 | RNA | Cancer 12 | 562.8 | 1.95 | RNA |
| paracancerous 6 | 300 | 1.93 | RNA | Cancer adjacent 12 | 435.6 | 2.06 | RNA |

Example 2 Fluorescent Quantitative PCR

1. Obtaining cDNA by Reverse Transcription
Use the Promega M-MLV kit, for details, see the kit instructions.
2. Designing Primer

TABLE 2

Fluorescent quantitative PCR primers

| target gene | Accession | Upstream primer sequences | Downstream primer sequences | Amplified fragment size |
|---|---|---|---|---|
| MKI67 | NM_002417 | GCTTCTCTTCTGACCCTGATG (SEQ ID NO. 1) | CTGATGGTTGAGGCTGTTCC (SEQ ID NO. 2) | 213 bp |
| EGFR | NM_005228 | GGTGACCGTTTGGGAGTT (SEQ ID NO. 3) | CCTGAATGACAAGGTAGCG (SEQ ID NO. 4) | 245 bp |
| TP53 | NM_001126112 | GAGGTTGGCTCTGACTGTACC (SEQ ID NO. 5) | TCCGTCCCAGTAGATTACCAC (SEQ ID NO. 6) | 133 bp |
| ERBB2 | NM_004448 | GGAAGGTGAAGGTGCTTGGATC (SEQ ID NO. 7) | TAGGGCATAAGCTGTGTCACCAG (SEQ ID NO. 8) | 247 bp |
| PCNA | NM_002592 | TGAAGCACCAAACCAGGAG (SEQ ID NO. 9) | GAAGGCATCTTTACTACACAGC (SEQ ID NO. 10) | 114 bp |
| ERH | NM_004450 | GCTGCTGTAGCGAAGAGA (SEQ ID NO. 11) | GGCTGGTATGTCTGGGTAT (SEQ ID NO. 12) | 270 bp |
| GAPDH | | TGACTTCAACAGCGACACCCA (SEQ ID NO.13) | CACCCTGTTGCTGTAGCCAAA (SEQ ID NO. 14) | 121 bp |

3. Detecting Real-Time PCR

12 μl of the reaction system was configured with TAKARA Fluorescent Quantitative Reagent (cat. No. DRR041B): each tube was added SYBR premix ex taq 6 μl; Primer mix (57M) 0.3 μl; Reverse transcript cDNA 0.6 μl; RNase-free water 5.1 μl. Two-step Real-time PCR: predegeneration 95 C 30 s; 40 cycles (denaturation 95° C. 5 s; annealing and extension 60° C. 30 s). And made the dissolution curve.

4. Analyzing Data

The results showed that the real-time quantitative PCR amplification curve had good overall parallelism, indicating that the amplification efficiency of each reaction tube was similar, the inflection point of the amplification curve was clear, the limit is flat and there was no upward trend, and the slope of the curve index period was large, indicating that the amplification efficiency was higher; The dissolution profile of the amplification product was a single peak, indicating that the amplification product was unique, and was a specific amplification; Relative quantification formula of RT-PCR: $\Delta Ct$=target gene Ct value-GAPDH Ct value; $-\Delta\Delta Ct$=same number of paracancerous tissue $\Delta Ct$–the same serial number of each sample $\Delta Ct$; $2^{-\Delta\Delta Ct}$ reflected the relative expression levels of target genes in the same serial cancer tissue samples relative to the paracancerous tissue samples. The relative expression levels of ERH, MKI67, EGFR, ERBB2, TP53 and PCNA genes in 12 pairs of bladder cancer tissues and paracancerous tissues were calculated.

TABLE 3

Fluorescent Quantitative Detection of Gene Expression in Bladder Cancer and Paracancerous Tissues

| Samples | GAPDH Ct | ERH Ct | ΔCt | MKI67 Ct | ΔCt | EGFR Ct | ΔCt | ERBB2 Ct | ΔCt | TP53 Ct | ΔCt | PCNA Ct | ΔCt |
|---|---|---|---|---|---|---|---|---|---|---|---|---|---|
| Cancer1 | 14.18 | 22.27 | 8.09 | 24.97 | 10.79 | 20.27 | 6.09 | 19.77 | 5.59 | 21.3 | 7.12 | 20.33 | 6.15 |
| Paracancerous 1 | 17.62 | 26.55 | 8.93 | 23.73 | 6.11 | 24.3 | 6.68 | 24.85 | 7.23 | 25.54 | 7.92 | 24.22 | 6.6 |
| Cancer 2 | 14.97 | 20.92 | 5.95 | 24.67 | 9.7 | 18.83 | 3.86 | 18.65 | 3.68 | 19.58 | 4.61 | 20.61 | 5.64 |
| Paracancerous 2 | 17.26 | 25.48 | 8.22 | 23.08 | 5.82 | 23.45 | 6.19 | 24.18 | 6.92 | 24.58 | 7.32 | 23.73 | 6.47 |

TABLE 3-continued

Fluorescent Quantitative Detection of Gene Expression in Bladder Cancer and Paracancerous Tissues

| Samples | GAPDH Ct | ERH Ct | ΔCt | MKI67 Ct | ΔCt | EGFR Ct | ΔCt | ERBB2 Ct | ΔCt | TP53 Ct | ΔCt | PCNA Ct | ΔCt |
|---|---|---|---|---|---|---|---|---|---|---|---|---|---|
| Cancer 3 | 15.77 | 22.6 | 6.83 | 25.86 | 10.09 | 21.81 | 6.04 | 21.91 | 6.14 | 21.95 | 6.18 | 20.97 | 5.2 |
| Paracancerous 3 | 18.2 | 25.81 | 7.61 | 26.22 | 8.02 | 23.58 | 5.38 | 23.75 | 5.55 | 25.15 | 6.95 | 24.73 | 6.53 |
| Cancer 4 | 17.27 | 25.91 | 8.64 | 21.1 | 3.83 | 25.08 | 7.81 | 27.42 | 10.15 | 22.18 | 4.91 | 25.44 | 8.17 |
| Paracancerous 4 | 16.88 | 23.99 | 7.11 | 25.1 | 8.22 | 22.27 | 5.39 | 23.48 | 6.6 | 23.26 | 6.38 | 21.84 | 4.96 |
| Cancer 5 | 15.81 | 22.71 | 6.9 | 23.03 | 7.22 | 21.65 | 5.84 | 21.88 | 6.07 | 22.58 | 6.77 | 21.78 | 5.97 |
| Paracancerous 5 | 15.44 | 24.28 | 8.84 | 23.81 | 8.37 | 23.79 | 8.35 | 21.49 | 6.05 | 24.83 | 9.39 | 20.94 | 5.5 |
| Cancer 6 | 17.81 | 25.84 | 8.03 | 23.29 | 5.48 | 26.28 | 8.47 | 26.83 | 9.02 | 25.49 | 7.68 | 23.86 | 6.05 |
| Paracancerous 6 | 18.68 | 28.67 | 9.99 | 24.45 | 5.77 | 26.6 | 7.92 | 25.79 | 7.11 | 28.11 | 9.43 | 23.62 | 4.94 |
| Cancer 7 | 16.33 | 23.9 | 7.57 | 24.12 | 7.79 | 21.65 | 5.32 | 21.71 | 5.38 | 22.11 | 5.78 | 21.97 | 5.64 |
| Paracancerous 7 | 15.52 | 23.56 | 8.04 | 24.23 | 8.71 | 22.21 | 6.69 | 21.64 | 6.12 | 24.31 | 8.79 | 21.62 | 6.1 |
| Cancer 8 | 17.28 | 24.22 | 6.94 | 24.65 | 7.37 | 23.13 | 5.85 | 22.19 | 4.91 | 22.5 | 5.22 | 23.25 | 5.97 |
| Paracancerous 8 | 16.46 | 23.03 | 6.57 | 23.25 | 6.79 | 22.29 | 5.83 | 21.71 | 5.25 | 22.12 | 5.66 | 21.97 | 5.51 |
| Cancer 9 | 18.91 | 26.8 | 7.89 | 24.23 | 5.32 | 26.74 | 7.83 | 28.07 | 9.16 | 25.79 | 6.88 | 25.11 | 6.2 |
| Paracancerous 9 | 17.2 | 23.58 | 6.38 | 24.53 | 7.33 | 23.23 | 6.03 | 22.82 | 5.62 | 23.76 | 6.56 | 21.15 | 3.95 |
| Cancer 10 | 15.68 | 22.79 | 7.11 | 24.76 | 9.08 | 20.91 | 5.23 | 24.66 | 8.98 | 23.46 | 7.78 | 21.29 | 5.61 |
| Paracancerous 10 | 16.01 | 23.9 | 7.89 | 23.89 | 7.88 | 24.47 | 8.46 | 24.79 | 8.78 | 24.27 | 8.26 | 23.14 | 7.13 |
| Cancer 11 | 16.83 | 23.77 | 6.94 | 23.71 | 6.88 | 23.86 | 7.03 | 22.61 | 5.78 | 24.25 | 7.42 | 23.29 | 6.46 |
| Paracancerous 11 | 16.76 | 23.28 | 6.52 | 25.27 | 8.51 | 22.52 | 5.76 | 23.01 | 6.25 | 26.73 | 9.97 | 22.42 | 5.66 |
| Cancer 12 | 15.22 | 21.64 | 6.42 | 24.63 | 9.41 | 20.84 | 5.62 | 21.23 | 6.01 | 27.05 | 11.83 | 20.24 | 5.02 |
| Paracancerous 12 | 16.85 | 24.16 | 7.31 | 24.86 | 8.01 | 23.63 | 6.78 | 24.11 | 7.26 | 24.22 | 7.37 | 23.76 | 6.91 |

Further, using MKI67, EGFR, ERBB2, TP53, and PCNA as marker genes, the influence of the sample on gene expression was corrected.

TABLE 4

| Gene | Cancer 1 | Cancer 2 | Cancer 3 | Cancer 4 | Cancer 5 | Cancer 6 | Cancer 7 | Cancer 8 | Cancer 9 | Cancer 10 | Cancer 11 | Cancer 12 |
|---|---|---|---|---|---|---|---|---|---|---|---|---|
| MKI67 |  |  |  | ✓ | ✓ | ✓ | ✓ |  | ✓ |  | ✓ |  |
| EGFR | ✓ | ✓ |  |  | ✓ |  | ✓ |  |  | ✓ |  | ✓ |
| ERBB2 | ✓ | ✓ |  |  |  |  | ✓ | ✓ |  |  | ✓ | ✓ |
| TP53 | ✓ | ✓ | ✓ | ✓ | ✓ | ✓ | ✓ | ✓ |  | ✓ | ✓ |  |
| PCNA | ✓ | ✓ | ✓ |  |  |  | ✓ |  |  | ✓ |  | ✓ |
| Reference degree | Strong | Strong | Weak | Weak | Strong | Weak | Strong | Weak | No | Strong | Strong | Strong |
| ERH | ✓ | ✓ | ✓ |  | ✓ | ✓ | ✓ |  |  | ✓ |  | ✓ |

The "✓" of Marker gene indicated that the gene's expression level in this sample was consistent with known reports. The weak reference referred to the sample with the positive marker number=2, the strong reference referred to the sample with the positive marker number ≥3, and "No" referred to a sample with a positive marker of <2, which was not acted as a reference.

According to the detection of the expression of 12 pairs of sample candidate genes, 7 pairs of samples were strong reference samples. The ERH gene was up-regulated in 6 pairs of strong reference samples and 2 pairs of weak reference samples, indicating that the ERH gene had a good correlation with bladder cancer. The combined detection of ERH gene and MKI67, EGFR, ERBB2, TP53 and PCNA would further improve the detection accuracy of bladder cancer.

Example 3 RNA Interference Lentiviral Vector Preparation of ERH Gene

1. RNA Interference Target Design and Double-Stranded DNA Oligo Preparation

ERH (NM_004450 Homo sapiens Homo sapiens enhancer of rudimentary homolog (ERH), mRNA), according to the principles of RNA interference sequence design, the ERH gene was used as a template to design multiple 19-21 nt RNA interference target sequences. After the design software evaluates the assay, the following sequence was selected as the interference target:

Target sequence:

(SEQ ID NO. 15)
CTGGTTTACCGAGCTGATA

The shRNA interference sequences were designed based on the selected target sequences and appropriate restriction endonuclease cutting sites were added at both ends to complete vector construction. In addition to this, a TTTTT termination signal was added at the 3' end of the positive strand and a termination signal complementary sequence was added at the 5' end of the reverse strand. After the design was completed, Czech company synthesized single-stranded DNA oligo.

TABLE 5

| 5' additional base | STEM | Loop | STEM | 3' Additional base |
|---|---|---|---|---|
| CCGG | GCCTGGTTTA CCGAGCTGAT A | CTCGA G | TATCAGCTCG GTAAACCAGG C | TTTTTG |

TABLE 5-continued

| 5'<br>additional<br>base | STEM | Loop | STEM | 3'<br>Additional<br>base |
|---|---|---|---|---|
| AATTCAAAA<br>A | GCCTGGTTTA<br>CCGAGCTGAT<br>A | CTCGA<br>G | TATCAGCTCG<br>GTAAACCAGG<br>C | |

Note: CCGG: AgeI restriction site; AATTC: EcoRI restriction site; G: EcoRI restriction site complementary sequence.

The synthesized single-stranded DNA oligo powder was dissolved in annealing buffer (final concentration 100M) and bathed at 90° C. for 15 min. After spontaneous cooling to room temperature, double bonds with sticky ends were formed.

2. Linear Preparation of GV115 Vector

Figure 1:
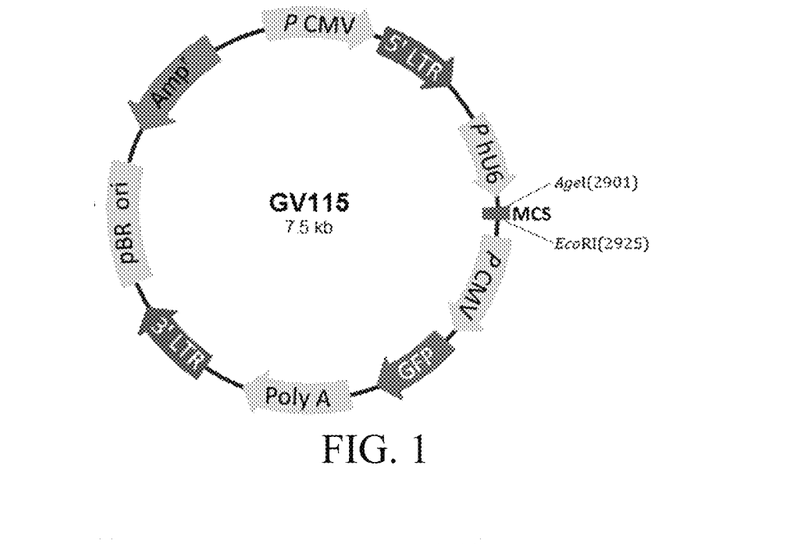
FIG. 1 shows the GV115 vector.

A 50 μl reaction system was prepared according to the NEB instructions, and the GV115 vector was double-enzymatically digested with AgeI and EcoRI (vector shown in FIG. 1) to linearize it (GV115 vector was provided by Shanghai GK Genentech Co., Ltd.). The reaction was performed at 37° C. (optimum temperature) for 1 h, and the target fragment was recovered by cutting the gel.

3. Construction of RNA Interference Lentiviral Vector

A 201 reaction system was prepared according to the Fermentas T4 DNA Ligase instructions and the double-stranded DNA oligo was ligated to the linearized vector. The reaction was performed at 16° C. for 1 h to 3 h, and the ligation product was named as psc2903, after which transformation experiments were performed. The ligation product was transformed into E. coli competent cells. Positive clones were identified by PCR and the primers were identified as follows:

Upstream Primer:

```
                                    (SEQ ID NO. 16)
        CCTATTTCCCATGATTCCTTCATA
```

Downstream primers:

```
                                    (SEQ ID NO. 17)
        GTAATACGGTTATCCACGCG
```

Figure 2:
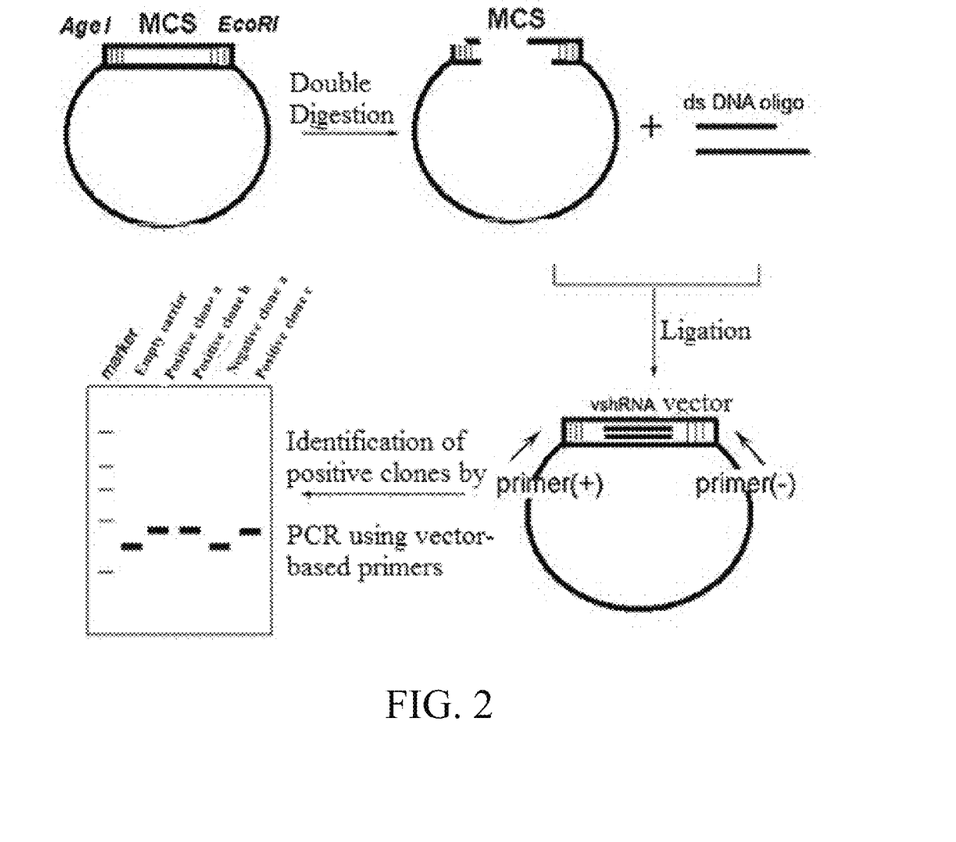
FIG. 2 shows the construction of RNA interference vectors and the identification of positive clones.

The positive clones were sequenced with the identification primers, and the clones with the same sequence as the target sequence were selected for plasmid extraction. The schematic diagram of the RNA interference vector construction and positive clone identification was shown in FIG. 2.

Example 4 Detection of Target Gene Expression in Target Cells by RT-PCR

The RNA of human bladder cancer cell lines 5637 and T24 was extracted by using TRIzol method, and the mRNA abundance of ERH gene in human bladder cancer cells 5637 and T24 was detected by RT-PCR. Referred to Example 2 for the specific procedure. The results were shown in Table 6. Both bladder cancer cells expressed ERH gene with high abundance.

TABLE 6

| Sample | ΔCt | STDEV |
|---|---|---|
| 5637 | 2.61 | 0.040 |
| T24 | 4.57 | 0.170 |

Remarks:
ΔCt = target gene Ct value − reference gene Ct value;
when the ΔCt value ≤12, the gene expression abundance in the cell is high;
when 12 < ΔCt value <16, the gene expression abundance in the cell is medium;
When the ΔCt value ≥16, the gene expression abundance in this cell is low.

Example 5 Construction and Packaging of RNAi Lentiviral Vector

1. Vector Digestion

Figure 3:
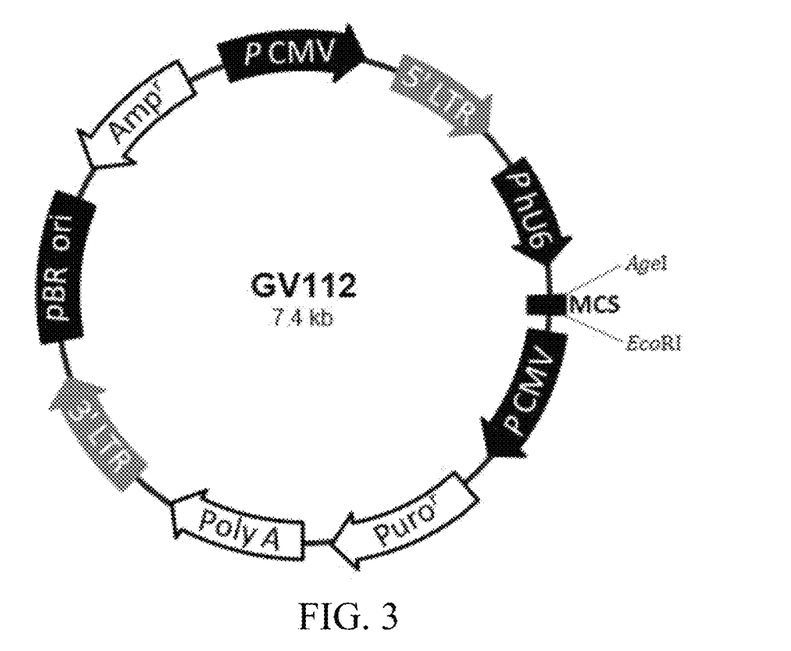
FIG. 3 shows the GV112 vector.

The vector GV112 was digested with restriction enzyme (AgeI, EcoRI enzyme) (provided by Shanghai GK Gene Chemical Technology Co., Ltd., the vector map was shown in FIG. 3), and the enzyme digestion system was: 10× buffer, 5 μl; 1 each of AgeI, EcoRI enzyme (10 U/μl); 2 μg of the purified vector plasmid; buffered with deionized water to 50 μl. After reacting at 37° C. for 3 hours or overnight, a linearized vector was obtained and subjected to agarose gel electrophoresis to recover the target band.

2. Synthesis of the Target Fragment

Synthetic single-stranded primers

```
GV112-ERH-1:
                                    (SEQ ID NO. 18)
5'-CCGGGCCTGGTTTACCGAGCTGATACTCGAG

TATCAGCTCGGTAAACCAGGC TTTTTG-3'

GV112-ERH-2:
                                    (SEQ ID NO. 19)
5'-AATTCAAAAAGCCTGGTTTACCGAGCTGATACTCGAG

TATCAGCTCGGTAAACCAGGC-3'
```

The primers were annealed to form double-stranded DNA, after synthesis, the paired primer powders were dissolved in annealing buffer and bathed at 90° C. for 15 min, and then naturally cooled to room temperature. GV112-ERH-1 and GV112-ERH-2 were paired.

3. Connecting Annealed Product and Vector

The reaction system was formulated with a linearized vector and an annealing product, and the double-encoded linearized vector and the annealed double-stranded DNA were ligated by T4 DNA ligase, ligated at 16° C. for 1-3 h, or ligated overnight.

4. Conversion

The reaction product was added to competent cells of E. coli and mixed under light bollards and placed on ice for 30 min. Heat shock at 42° C. for 90 s and incubate in ice bath for 2 min. The LB medium was added and the plate was shaken at 37° C. for 1 h. The appropriate amount of broth was evenly spread on the plate containing the corresponding antibiotics, and incubating in a constant temperature incubator for 12-16 h.

5. Colony PCR Identification

Identification primers:
Upstream Primer:

```
                                    (SEQ ID NO. 20)
        5'-CCATGATTCCTTCATATTTGC-3'
```

Downstream primer:

5'-GTAATACGGTTATCCACGCG-3' (SEQ ID NO. 21)

A single clone on the plate was picked for PCR identification. The identification primers were SEQ ID NO.20 and SEQ ID NO.21. The positive clones were sequenced and the results were analyzed. The correct cloning bacteria solution was expanded and extracted to obtain high-purity plasmids for downstream viral packaging.

Example 6 Lentiviral Infects Target Cells and Gene Knockout Efficiency

1. Preparing the Target Cells

Removed the human bladder cancer cell T24 cryovial from the liquid nitrogen tank and quickly placed it in a 37° C. water bath and shook it to thaw as soon as possible. After completely thawing, centrifuged at 1300 rpm for 3 min. Disinfected the freezing tube and moved to biological safety cabinet; aspirated the supernatant, resuspending the cells by adding 1 mL of fresh complete medium (1640+10% FBS), and inoculated the cell suspension to 6-cm dish containing 3 mL of complete medium. In the dish, gently shook it and place it in a 37° C., 5% $CO_2$ incubator. After 24 hours, replaced the culture solution with another culture medium and continue the culture until the cell confluence reached 80% to maintain the cells in a good state of growth.

2. Cell Lentivirus Infection

The cells in the logarithmic growth phase were digested with trypsin, and the complete culture medium was made into 3-5×$10^4$ cells/mL cell suspension, and the appropriate number of cells was inoculated into the culture plate (recommended 6-well plate 2 mL inoculation area, 1 mL change volume), continued to culture to ensure that the amount of plating reaches about 15-30% when infected; replaced the infection medium, add the optimal amount of virus for infection (control group virus titer 5×$10^8$ TU/ml, the amount of infection 4 μl; the virus titer of experimental group was 1×$10^9$ TU/ml and the infection dose was 2 μl). The optimal time after infection was chosen to change to regular culture medium and continue culture (usually about 8-12 h after infection).

Observing the Cells State and Infection Efficiency after Infection

The cells were in good condition and there was no large number of deaths, especially in the control group (normal target cells, plus negative control virus infected cell group, shCtrl) and experimental groups (normal target cells, Cell group infected with shRNA of ERH gene, shERH) had a similar cell state; the fluorescent-tagged lentivirus infected about 72 hours after infection, the expression of the reporter gene was observed under a fluorescent microscope, the fluorescence rate was a positive infection rate.

3. Gene Knockdown Efficiency

Total RNA was extracted from the control group and the experimental group and RT-PCR was performed after reverse transcription. The specific procedures referred to the foregoing embodiments.

4. Experimental Results

Figure 4:
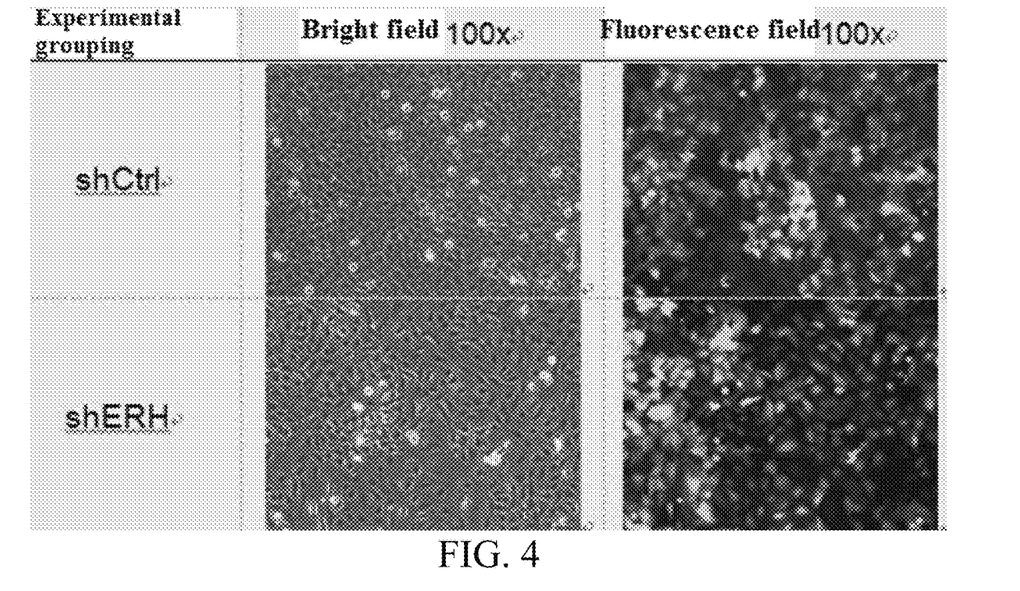
FIG. 4 shows a microscopic fluorescence image after lentivirus infection.

In the control group and experimental group, the objective virus was infected by lentivirus after 72 hours under the microscope. The observation results showed that the cell infection efficiency reached 80% or more, and the cell state was normal. The results were shown in FIG. 4.

Figure 5:
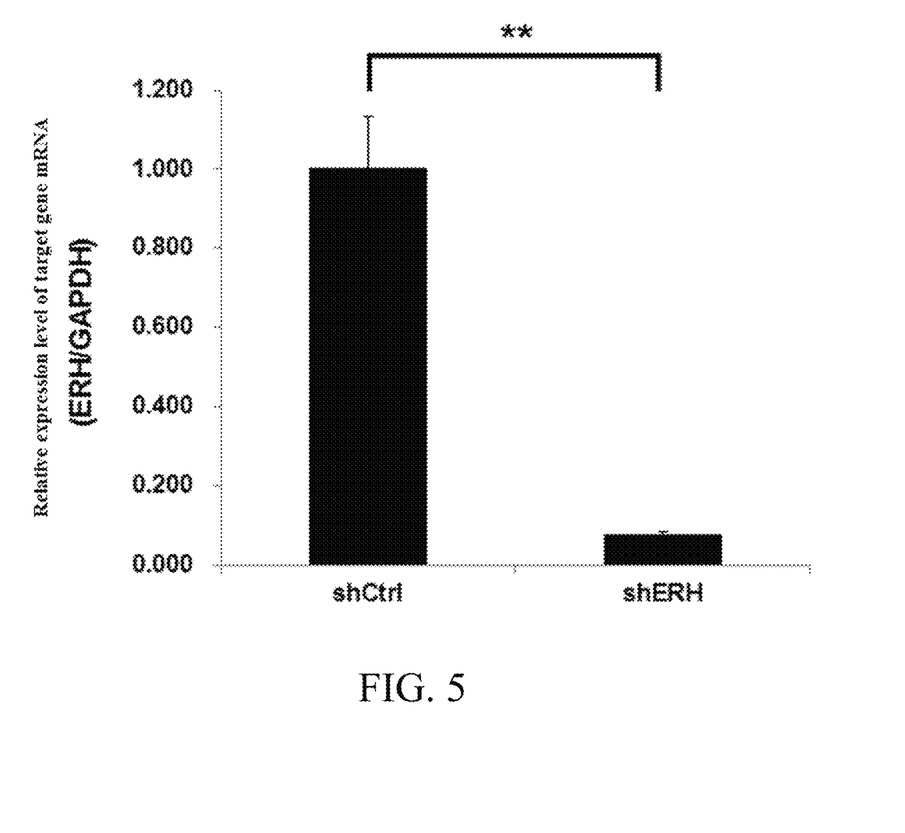
FIG. 5 is a graph showing the ERH gene knockdown efficiency of mRNA levels after lentivirus infection.

Quantitative PCR results showed that after shRNA lentivirus infection, the expression level of ERH mRNAin experimental group T24 cells was inhibited ($p<0.05$), knockdown efficiency reached 92.1%, as shown in FIG. 5.

Example 7 Celigo Cell Count Detects Growth

1. Experimental Procedure:
1) After the trypsin digestion of the control and experimental cells in the logarithmic growth phase, the complete medium was resuspended into a cell suspension and counted;
2) The plating cell density was determined by the speed of cell growth (most cell plating was set at 2000 cell/well). For each group of 3 wells, the culture system was 100 L/well. During the plating process, it was necessary to ensure that the number of cells added per well was the same, 37° C., 5% $CO_2$ incubator;
3) Starting from the second day after plating, Celigo detected the plate once a day and continuously detected the plate for 3-5 days;
4) Accurately calculated the number of cells with green fluorescence in each scanning well by adjusting the input parameters of the analysis settings; performed statistical plotting of the data and drew a 5 days cell proliferation curve.

2. Data Analysis and Experimental Results

Figure 6:
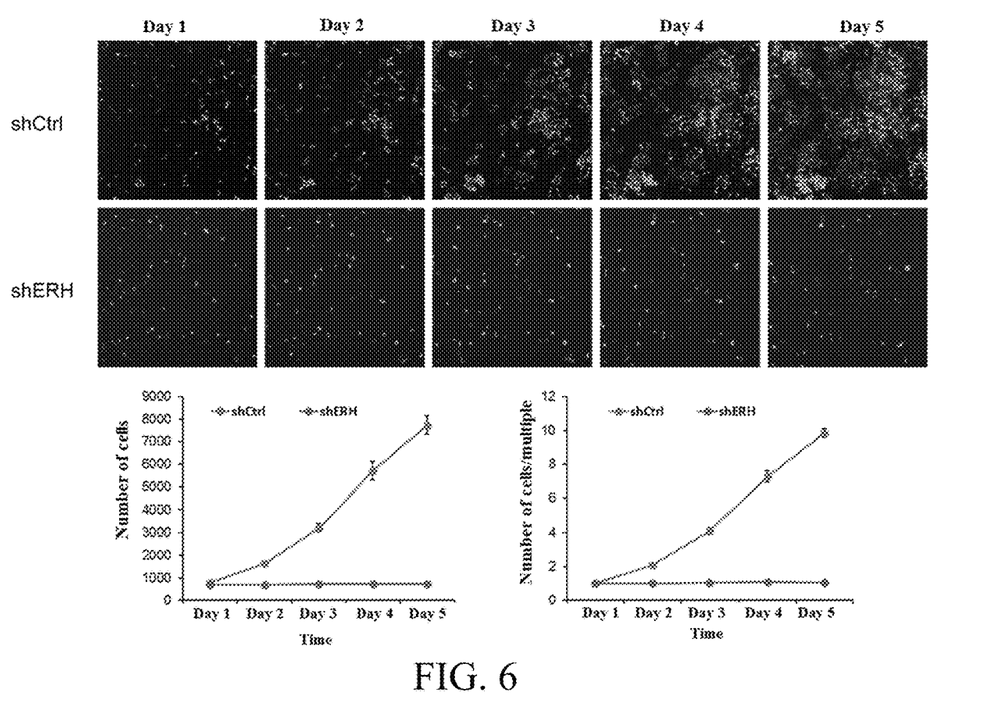
FIG. 6 is a graph showing the effects of ERH gene knockdown on cell proliferation detected by Celigo.

According to the cell count value and time point, the cell growth curve based on the cell count value was plotted, and the ratio of the cell count value at each time point of each group of cells to the cell count value of the first day was calculated, and the proliferation of the cells at each time point was obtained. In multiples, a growth curve based on the cell proliferation factor was drawn based on the multiplying factor and the time point, as shown in FIG. 6. The results showed that the proliferation of shERH cells was significantly inhibited compared with the shCtrl group, indicating that knockdown of ERH affected cell proliferation.

Example 8 Brdu Detection

BrdU could be competitively incorporated into the S-phase single-stranded DNA nucleotide sequence in place of thymidine, using the antibody ligase or fluorescein as an indicator system to label Brdu, and when Brdu was incorporated in cells that were actively dividing, Brdu-containing cells could be detected and used to determine the number of cells. The absorbance (OD value) was measured with a microplate reader at a wavelength of 450 nm. The level of OD was used to reflect the number of synthetic DNA cells, reflecting the amount of cells that were in the proliferative state.

Figure 7:
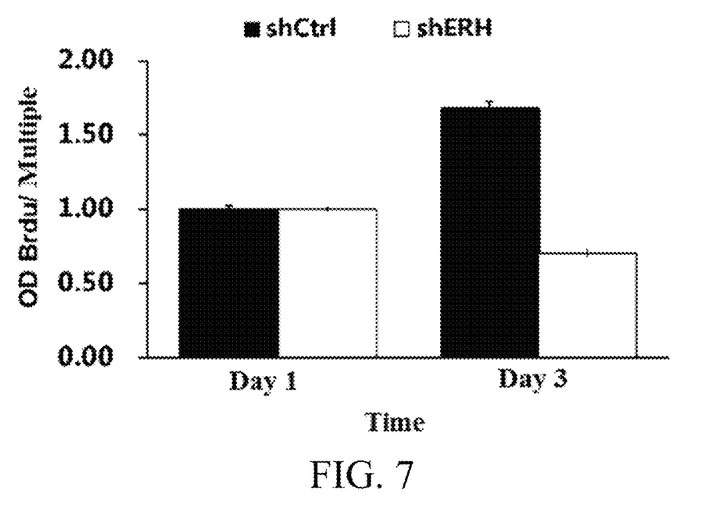
FIG. 7 is a graph showing the effects of ERU gene knockdown on cell proliferation detected by BRDU.

According to Example 6, the target cells of the control group and the experimental group were infected with lentivirus and subjected to Brdu assay. For the specific experimental procedure, referred to the instructions of Roche Brdu kit (article number 11647229001). The experimental results showed that compared with the shCtrl control group, the proliferation of cells in the shERH experimental group was slowed ($P<0.05$ on the first day), as shown in FIG. 7 (OD450/fold was the OD450 multiple of day 1 and day 3 of each experimental group relative to day 1, indicating the multiplier for each day).

Example 9 Apoptosis Detection

According to Example 6, the cells infected with the lentivirus in the control group and the experimental group were passaged on the 4th day after the cell lentivirus infection, and on the 5th day, the degree of cell fusion was 85%. For specific procedures, referred to the eBioscience Apoptosis Kit (Art. No. 88-8007) instructions.

The results showed that shRNA lentivirus infected T24 cells. After 5 days of culture, the average percentages of apoptotic cells in the control (shCtrl) and experimental (shERH) groups were 4.21% and 11.03%, respectively. Compared with the control group, the number of apoptotic cells in the shERH group increased (P<0.05).

Example 10 Clone Formation Assay

1. Experimental Procedure
(1) Preparing post-infectious cells: the objective cells were infected with lentivirus in the control group and the experimental group according to Example 6, and the cells in each experimental group in the logarithmic growth phase were trypsinized and resuspended in the complete culture medium to prepare a cell suspension, and count.
(2) Seeding the cells: each experimental group was inoculated with 400-1000 cells/well (determined according to cell growth) in a 6-well plate culture plate, and 3 replicate wells were set in each experimental group.
(3) Further culturing the inoculated cells in the incubator for 14 days or the number of cells in most of the individual clones was greater than 50, and the medium was changed and observed every 3 days.
(4) Photographing the cell clones under a fluorescence microscope before the termination of the experiment, and the cells were washed once with PBS.
(5) Adding 1 mL of 4% paraformaldehyde per well, fixed the cells for 30-60 min, and washed cells once with PBS.
(6) Adding 500 µL of clean, non-impurity GIEMSA dye solution to each well and stained the cells for 10-20 min.
(7) Washing the cells several times with ddH$_2$O, air dried, took a photo with a digital camera, and counted the clones.

2. Experimental Results

Figure 8:
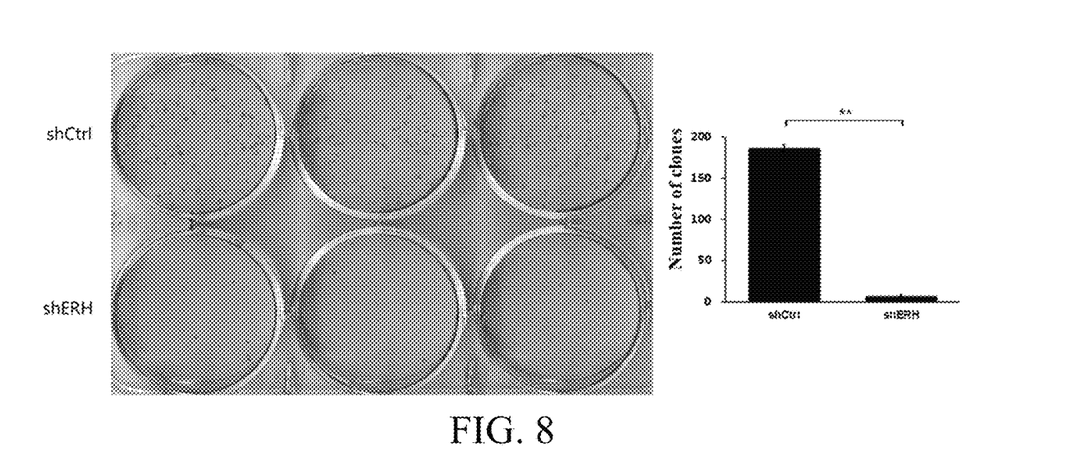
FIG. 8 is a graph detecting the effect of ERH gene ablation on cell clone formation.

The ability of the cells to grow tumorigenicity after lentivirus infection was demonstrated by the ability of the cells to colonize on the cell culture plate after infection. After shRNA lentivirus infection of T24 cells, the number of clones in the shERH group was significantly reduced compared with the shCtrl group (P<0.05), See FIG. 8 for details.

Example 11 MTT Detection

According to Example 6, the target cells of the control group and the experimental group were infected with lentivirus, and the detection was performed 24 to 120 hours after the plate was separated. The specific procedure was followed by the MTT kit (article number: JT343) instructions of Genview.

Figure 9:
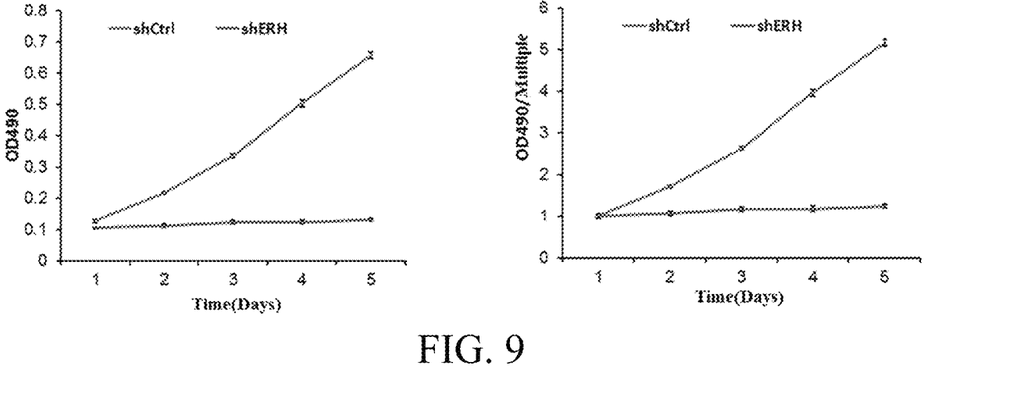
FIG. 9 is a graph showing the efficacy of ERH knockdown on cell proliferation detected by MTT.

The OD490/fold was the OD490 multiple of the first day to the fifth day of each experimental group relative to the first day, indicating the multiple of proliferation on each day. FIG. 9 showed the time-dependent change in the absorbance change of the shERH group and the control group (shCtrl) in the plate reader at a wavelength of 490 nm. OD490 here reflected the number of viable cells. The results showed that the proliferation of cells in the shERH group was slower compared to the shCtrl group.

Example 12 Detection of Targets by Western Blot Reduces Expression of Target Gene Proteins 1. Total Protein Extraction Lentivirus infection was performed in the control group and the experimental group, and the objective cells in a good growth state after infection with lentivirus were collected, protein was extracted, and the protein concentration was determined by the BCA method (Biyuntian BCA Protein Assay Kit, Cat. No. P0010S). Adjusted the protein concentration of each sample to 2 µg/L and stored at −80° C. until use.

2. SDS-PAGE

According to the size of the protein molecular weight, a concentration of 10% separation gel and 5% concentration gel was formulated. After the gel had solidified, removed the comb, washed the sample well with electrophoresis buffer, and loaded the prepared sample. Stacking gel 80 mA for 20 min; separation gel 120 mA for 1 h.

3. Immunoblotting

After the electrophoresis was completed, the protein was transferred to a PVDF membrane by using a transfer electrophoresis apparatus (Bio-Rad, Richmoad, CA) and electroconversion at 300 mA under a constant current of 4° C. for 120 min.

4. Immunological Coloration
1) Blocking: Blocked PVDF membranes at room temperature for 1 h or 4° C. overnight with blocking solution (containing 5% skim milk in TBST);
2) Incubating primary antibody: blocking antibody dilution (primary antibody Sigma Mouse Anti-Flag, Catalog No. F1804, 1:2000, primary Santa-Cruz Mouse anti-GAPDH Cat. No. sc-32233, 1:2000), and then sealed PVDF membrane incubate at room temperature for 2 h or 4° C. overnight;
3) Washing the membrane: TBST washed the membrane 3 times, each 10 min;
4) Incubating secondary antibody: The corresponding secondary antibody (second antibody Santa-Cruz Goat Anti-Mouse IgG cat. No. sc-2005, 1:2000) was diluted with a blocking solution, and the PVDF membrane was incubated at room temperature for 2 hours.
5) Washing film: TBST washed 3 times, each 10 min;
6) X-ray developing: Using Thermo's Pierce™ ECL Western Blotting Substrate Kit.
   (1) Placed the PVDF membrane on the prefabricated fresh-keeping film, and mixed the liquid A and B in a ratio of 1:40. The mixture was uniformly added to the PVDF membrane and protected from light for 3-5 minutes.
   (2) Took out the membrane, drained the excess ECL substrate reaction solution slightly, put it into the cassette, covered with plastic wrap (to avoid air bubbles), put the X-ray film (to avoid the movement of the X-ray film), closed the cassette, and exposed 1-2 min.
   (3) Took out the X-ray film, put it into the developer solution, removed it after about 1 minute, rinsed it in clean water for a few seconds, and put it into the fixing solution for at least 2 minutes.
   (4) Removed the X-ray film, dried it, and analyzed.

5. Experimental Results

Figure 10:
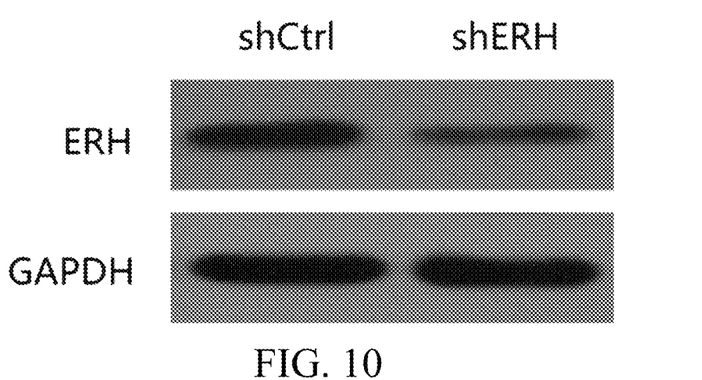
FIG. 10 is a graph showing the target reduction ERH gene protein expression level detected by WB.

Western Blot results showed that the target vector shERH had a significant inhibitory effect on the expression of the target gene, and thus the target of the present invention was an effective target. The specific results were shown in FIG. 10.

What is claimed is:

1. A method of treating or preventing bladder cancer comprising the step of reducing expression of ERH gene or protein in a subject in need thereof, wherein the expression of the ERH gene or protein is downregulated by introducing interfering RNA targeting ERH.

2. The method of claim 1, wherein the target sequence of the interfering RNA targeting ERH is SEQ ID NO.15.

3. The method of claim 2, wherein the sequences of the interfering RNA are SEQ ID NO.18 and SEQ ID NO.19.

* * * * *

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: upstream MK167 primer

<400> SEQUENCE: 1
gcttctcttc tgaccctgat g                                          21

<210> SEQ ID NO 2
<211> LENGTH: 20
<212> TYPE: DNA
<213> ORGANISM: Artificial Sequence
<220> FEATURE:
<223> OTHER INFORMATION: downstream MK167 primer

<400> SEQUENCE: 2
ctgatggttg aggctgttcc                                            20

<210> SEQ ID NO 3
<211> LENGTH: 18
<212> TYPE: DNA
<213> ORGANISM: Artificial Sequence
<220> FEATURE:
<223> OTHER INFORMATION: upstream EGFR primer

<400> SEQUENCE: 3
ggtgaccgtt tgggagtt                                              18

<210> SEQ ID NO 4
<211> LENGTH: 19
<212> TYPE: DNA
<213> ORGANISM: Artificial Sequence
<220> FEATURE:
<223> OTHER INFORMATION: downstream EGFR primer

<400> SEQUENCE: 4
cctgaatgac aaggtagcg                                             19

<210> SEQ ID NO 5
<211> LENGTH: 21
<212> TYPE: DNA
<213> ORGANISM: Artificial Sequence
<220> FEATURE:
<223> OTHER INFORMATION: upstream TP53 primer

<400> SEQUENCE: 5
gaggttggct ctgactgtac c                                          21

<210> SEQ ID NO 6
<211> LENGTH: 21
<212> TYPE: DNA
<213> ORGANISM: Artificial Sequence
<220> FEATURE:
<223> OTHER INFORMATION: downstream TP53 primer

<400> SEQUENCE: 6
tccgtcccag tagattacca c                                          21

<210> SEQ ID NO 7
<211> LENGTH: 22
<212> TYPE: DNA
<213> ORGANISM: Artificial Sequence

```
<220> FEATURE:
<223> OTHER INFORMATION: upstream ERBB2 primer

<400> SEQUENCE: 7
ggaaggtgaa ggtgcttgga tc                                            22

<210> SEQ ID NO 8
<211> LENGTH: 23
<212> TYPE: DNA
<213> ORGANISM: Artificial Sequence
<220> FEATURE:
<223> OTHER INFORMATION: downstream ERBB2 primer

<400> SEQUENCE: 8
tagggcataa gctgtgtcac cag                                           23

<210> SEQ ID NO 9
<211> LENGTH: 19
<212> TYPE: DNA
<213> ORGANISM: Artificial Sequence
<220> FEATURE:
<223> OTHER INFORMATION: upstream PCNA primer

<400> SEQUENCE: 9
tgaagcacca aaccaggag                                                19

<210> SEQ ID NO 10
<211> LENGTH: 22
<212> TYPE: DNA
<213> ORGANISM: Artificial Sequence
<220> FEATURE:
<223> OTHER INFORMATION: downstream PCNA primer

<400> SEQUENCE: 10
gaaggcatct ttactacaca gc                                            22

<210> SEQ ID NO 11
<211> LENGTH: 18
<212> TYPE: DNA
<213> ORGANISM: Artificial Sequence
<220> FEATURE:
<223> OTHER INFORMATION: upstream ERH primer

<400> SEQUENCE: 11
gctgctgtag cgaagaga                                                 18

<210> SEQ ID NO 12
<211> LENGTH: 19
<212> TYPE: DNA
<213> ORGANISM: Artificial Sequence
<220> FEATURE:
<223> OTHER INFORMATION: downstream ERH primer

<400> SEQUENCE: 12
ggctggtatg tctgggtat                                                19

<210> SEQ ID NO 13
<211> LENGTH: 21
<212> TYPE: DNA
<213> ORGANISM: Artificial Sequence
<220> FEATURE:
<223> OTHER INFORMATION: upstream GAPDH primer

<400> SEQUENCE: 13
tgacttcaac agcgacaccc a                                             21
```

<210> SEQ ID NO 14
<211> LENGTH: 21
<212> TYPE: DNA
<213> ORGANISM: Artificial Sequence
<220> FEATURE:
<223> OTHER INFORMATION: downstream GAPDH primer

<400> SEQUENCE: 14
caccctgttg ctgtagccaa a                                          21

<210> SEQ ID NO 15
<211> LENGTH: 19
<212> TYPE: DNA
<213> ORGANISM: Artificial Sequence
<220> FEATURE:
<223> OTHER INFORMATION: RNA interference target sequence

<400> SEQUENCE: 15
ctggtttacc gagctgata                                             19

<210> SEQ ID NO 16
<211> LENGTH: 24
<212> TYPE: DNA
<213> ORGANISM: Artificial Sequence
<220> FEATURE:
<223> OTHER INFORMATION: upstream clone identification primer

<400> SEQUENCE: 16
cctatttccc atgattcctt cata                                       24

<210> SEQ ID NO 17
<211> LENGTH: 20
<212> TYPE: DNA
<213> ORGANISM: Artificial Sequence
<220> FEATURE:
<223> OTHER INFORMATION: downstream clone identificaton primer

<400> SEQUENCE: 17
gtaatacggt tatccacgcg                                            20

<210> SEQ ID NO 18
<211> LENGTH: 58
<212> TYPE: DNA
<213> ORGANISM: Artificial Sequence
<220> FEATURE:
<223> OTHER INFORMATION: GV112-ERH-1 primer

<400> SEQUENCE: 18
ccgggcctgg tttaccgagc tgatactcga gtatcagctc ggtaaaccag gcttttg    58

<210> SEQ ID NO 19
<211> LENGTH: 58
<212> TYPE: DNA
<213> ORGANISM: Artificial Sequence
<220> FEATURE:
<223> OTHER INFORMATION: GV112-ERH-2 primer

<400> SEQUENCE: 19
aattcaaaaa gcctggttta ccgagctgat actcgagtat cagctcggta aaccaggc   58

<210> SEQ ID NO 20
<211> LENGTH: 21
<212> TYPE: DNA
<213> ORGANISM: Artificial Sequence
<220> FEATURE:
<223> OTHER INFORMATION: upstream identification primer

```
<400> SEQUENCE: 20
ccatgattcc ttcatatttg c                                              21

<210> SEQ ID NO 21
<211> LENGTH: 20
<212> TYPE: DNA
<213> ORGANISM: Artificial Sequence
<220> FEATURE:
<223> OTHER INFORMATION: downstream identification primer

<400> SEQUENCE: 21
gtaatacggt tatccacgcg                                                20

<210> SEQ ID NO 22
<211> LENGTH: 21
<212> TYPE: DNA
<213> ORGANISM: Artificial Sequence
<220> FEATURE:
<223> OTHER INFORMATION: oligonucleotide stem

<400> SEQUENCE: 22
gcctggttta ccgagctgat a                                              21

<210> SEQ ID NO 23
<211> LENGTH: 21
<212> TYPE: DNA
<213> ORGANISM: Artificial Sequence
<220> FEATURE:
<223> OTHER INFORMATION: oligonucleotide stem

<400> SEQUENCE: 23
tatcagctcg gtaaaccagg c                                              21

<210> SEQ ID NO 24
<211> LENGTH: 10
<212> TYPE: DNA
<213> ORGANISM: Artificial Sequence
<220> FEATURE:
<223> OTHER INFORMATION: oligonucleotide additional 5' base

<400> SEQUENCE: 24
aattcaaaaa                                                           10
```